(12) United States Patent
Nessel et al.

(10) Patent No.: US 10,092,697 B2
(45) Date of Patent: Oct. 9, 2018

(54) DRUG DELIVERY DEVICE WITH DRUG CONTAINER COMPRISING A SENSOR AND OPTICAL DATA TRANSMISSION SYSTEM

(71) Applicant: Sanofi-Aventis Deutschland GmbH, Frankfurt am Main (DE)

(72) Inventors: Christian Nessel, Frankfurt am Main (DE); Daniel Auernhammer, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 367 days.

(21) Appl. No.: 14/439,175

(22) PCT Filed: Oct. 25, 2013

(86) PCT No.: PCT/EP2013/072445
§ 371 (c)(1),
(2) Date: Apr. 28, 2015

(87) PCT Pub. No.: WO2014/067879
PCT Pub. Date: May 8, 2014

(65) Prior Publication Data
US 2015/0273145 A1    Oct. 1, 2015

(30) Foreign Application Priority Data
Oct. 29, 2012    (EP) .................................... 12190305

(51) Int. Cl.
*A61M 31/00*    (2006.01)
*A61M 5/172*    (2006.01)
(Continued)

(52) U.S. Cl.
CPC .............. *A61M 5/172* (2013.01); *A61J 1/062* (2013.01); *A61K 38/2278* (2013.01);
(Continued)

(58) Field of Classification Search
CPC ................ A61M 5/172; A61M 5/1456; A61M 5/14566; A61M 2205/3306;
(Continued)

(56) References Cited

U.S. PATENT DOCUMENTS 533,575 A    2/1895   Wilkens
5,226,895 A  7/1993   Harris
(Continued)

FOREIGN PATENT DOCUMENTS

EP    0937471 A2    8/1999
EP    0937476 A2    8/1999
(Continued)

OTHER PUBLICATIONS

English Translation of Notice of Reasons for Rejection issued in Japanese Patent Applicatiojn No. 2015-538475 dated Aug. 8, 2017.

*Primary Examiner* — Kevin C Sirmons
*Assistant Examiner* — Leah Swanson
(74) *Attorney, Agent, or Firm* — McCarter & English, LLP

(57) ABSTRACT

A container designed to contain a fluid medicament and adapted to cooperate with a delivery device for delivering the fluid medicament comprises an electrically operable sensor system for measuring at least one physical or chemical parameter value related to the container and/or fluid medicament therein, wherein the sensor system comprises an optical receiver designed to receive optical radiation energy and to transform said optical radiation energy into electrical energy for operating the sensor system.

18 Claims, 2 Drawing Sheets

(51) Int. Cl.
*A61M 5/145* (2006.01)
*A61M 5/168* (2006.01)
*A61M 5/24* (2006.01)
*A61M 5/315* (2006.01)
*A61K 38/28* (2006.01)
*A61J 1/06* (2006.01)
*H04B 10/80* (2013.01)
*A61K 38/22* (2006.01)
*A61K 38/26* (2006.01)
*H04B 10/114* (2013.01)

(52) U.S. Cl.
CPC .............. *A61K 38/26* (2013.01); *A61K 38/28* (2013.01); *A61M 5/1456* (2013.01); *A61M 5/14566* (2013.01); *A61M 5/16854* (2013.01); *A61M 5/24* (2013.01); *A61M 5/31511* (2013.01); *A61M 5/31515* (2013.01); *A61M 5/31525* (2013.01); *H04B 10/1141* (2013.01); *H04B 10/807* (2013.01); *A61G 2203/32* (2013.01); *A61M 2005/16863* (2013.01); *A61M 2205/15* (2013.01); *A61M 2205/332* (2013.01); *A61M 2205/3306* (2013.01); *A61M 2205/3324* (2013.01); *A61M 2205/3331* (2013.01); *A61M 2205/3368* (2013.01); *A61M 2205/3569* (2013.01); *A61M 2205/3592* (2013.01); *A61M 2205/50* (2013.01); *A61M 2205/8212* (2013.01); *A61M 2205/8293* (2013.01)

(58) Field of Classification Search
CPC .... A61M 2205/332; A61M 2205/3331; A61M 2205/3334; A61M 2205/3569; A61M 5/16854; A61M 5/24; A61M 5/31511; A61M 5/31515; A61M 5/31525; A61G 2203/32; A61J 1/062
See application file for complete search history.

(56) References Cited

U.S. PATENT DOCUMENTS

| | | | |
|---|---|---|---|
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,585,698 B1 | 7/2003 | Packman et al. | |
| 6,899,698 B2 | 5/2005 | Sams | |
| 6,936,032 B1 | 8/2005 | Bush, Jr. et al. | |
| 7,195,609 B2 | 3/2007 | Huegli | |
| 7,241,278 B2 | 7/2007 | Moller | |
| 7,330,550 B1* | 2/2008 | Johnson | H04L 9/0858 380/229 |
| 8,197,444 B1* | 6/2012 | Bazargan | A61M 5/16854 604/131 |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2008/0183122 A1 | 7/2008 | Fisher et al. | |
| 2008/0188813 A1 | 8/2008 | Miller et al. | |
| 2008/0308580 A1* | 12/2008 | Gaydos | A61M 5/14566 222/333 |
| 2009/0275916 A1 | 11/2009 | Harms et al. | |
| 2011/0295215 A1* | 12/2011 | Nielsen | A61M 5/31533 604/257 |

FOREIGN PATENT DOCUMENTS

| | | |
|---|---|---|
| EP | 2190506 B1 | 8/2011 |
| JP | 2008-516711 A | 5/2008 |
| WO | 9938554 A1 | 8/1999 |
| WO | 0110484 A1 | 2/2001 |
| WO | 2010000084 A1 | 1/2010 |
| WO | 2011032956 A2 | 3/2011 |

* cited by examiner

DRUG DELIVERY DEVICE WITH DRUG CONTAINER COMPRISING A SENSOR AND OPTICAL DATA TRANSMISSION SYSTEM

CROSS REFERENCE TO RELATED APPLICATIONS

The present application is a U.S. National Phase Application pursuant to 35 U.S.C. § 371 of International Application No. PCT/EP2013/072445 filed Oct. 25, 2013, which claims priority to European Patent Application No. 12190305.8 filed Oct. 29, 2012. The entire disclosure contents of these applications are herewith incorporated by reference into the present application.

FIELD OF INVENTION

The invention relates to a medicament delivery device for cooperating with a fluid medicament container where the medicament delivery device or the fluid medicament container comprises a sensor system being able to measure a physical or chemical parameter value relevant to the medicament or medicament dispensing and/or being able to communicate information about such a measured parameter value.

BACKGROUND

For the safe and reliable operation of a medicament delivery device delivering a fluid medicament it is essential to ensure that the correct dose size or volume flow of the fluid medicament is delivered to the patient. A potential problem in such a medicament delivery device is an occlusion anywhere in the outlet path from the drug container to the delivery point such as the tissue or vein of the patient. A further potential problem in such a medicament delivery device is the occurrence of a leak in the in the medicament container or along the fluid medicament delivery line. A safety system is therefore needed to sense if an occlusion or a leak occurs in the medicament delivery device in order to ensure the requested dose delivered to the patient.

U.S. Pat. No. 7,195,609 addresses the problem of detecting an occlusion or a leak by incorporating a sensor in the movable piston of a product container and connecting the sensor via wires for monitoring the pressure in the drug container.

EP 2 190 506 B1 discloses a medicament container for a fluid drug like a cartridge closed in one end with a moveable plunger or a flexible reservoir, wherein said container has a sensor to measure parameters related to the drug or drug delivery. Said sensor has an electrically operated transponder device to emit parameter values measured by the sensor in response to activation by a suitable field applied by external means. EP 2 190 506 B1 further discloses a medical delivery device configured to deliver a fluid drug from such a container that comprises control circuitry and such a sensor, wherein the control circuitry comprises activation means to provide a field suitable for such a sensor and further comprises a receiver to receive data from such a sensor.

SUMMARY

It is an object of the present invention to provide an improved container and/or an improved delivery device to monitor the delivery of a fluid medicament from a container.

It is a further object of the present invention to increase the flexibility of engineering and handling a delivery device adapted to cooperate with a medicament container while monitoring the delivery of a fluid medicament from the container.

Preferred embodiments of the invention are given in the dependent claims.

In accordance to a first aspect of the present invention, a container designed to contain a fluid medicament and adapted to cooperate with a delivery device for delivering the fluid medicament comprises an electrically operable sensor system. The sensor system is designed to measure at least one physical or chemical parameter value related to the container and/or the fluid medicament therein. Said sensor system comprises an optical receiver that is designed to receive optical radiation energy and to transform this optical radiation energy into electrical energy for operating the sensor system.

By using optical radiation energy for the power supply of the sensor system it is possible to relieve the sensor system from wires that otherwise would connect the sensor system with an electrical power supply outside the container. This increases the flexibility for engineering both the container and the delivery device that it is adapted for. Photoelectrical modules for transforming optical radiation energy into electrical energy are available at low cost, thus reducing the cost of goods for an solution according to the present invention.

Furthermore, such photoelectrical modules are available in miniaturized sizes so that the sensor system can be integrated in a silicon chip, thereby reducing the overall footprint of the sensor system advantageously.

Photoelectrical modules that operate for a wide range of optical radiation are available that greatly improve the robustness of the sensor system as it can be operated under less specific conditions relating to the supplying optical radiation source. According to an embodiment of the invention, it is possible to even use generic optical radiation sources like daylight or ceiling light.

In another embodiment of the invention, the optical receiver comprises an optical decoder designed to receive a first optical signal and to transfer the first optical signal into a first electrical signal processable by the sensor system. Thus, the sensor system may be controlled without further wires needed to transmit an electrical control signal. The advantage of greater flexibility for engineering is retained while a more versatile operation of the sensor is enabled. As an example, the sensor might be controlled in order to measure different physical or chemical parameters.

This embodiment of the invention is useful in that the first optical signal further on received by the optical decoder can not be disturbed by electromagnetic interference. Such electromagnetic interference is usually emitted by electrically operated devices as computers, mobile phones, electrical motors, electric switching devices as thermostats and many other devices. Such electromagnetic interference is further emitted by electric power lines, base stations of mobile phone networks or wireless communication systems. Due to the pervasiveness of such sources in a health care or home environment, the immunity of this embodiment of the invention to electromagnetic interference is particularly advantageous.

In a further useful embodiment of the invention, the optical decoder operates on the same optical radiation that is used for the power supply of the sensor system. This reduces the number of different electronic and photoelectrical parts required in the sensor system of the container as well as in the delivery device. In another embodiment of the invention, the optical decoder operates on a pulse-modulated or on an amplitude-modulated optical radiation, i.e. an optical radiation with varied brightness, whereas the energy of said optical radiation is transformed into electrical energy for the supply of the sensor system.

In a further embodiment of the invention, the sensor system comprises an optical transmitter designed to receive a second electrical signal and to transform the second electrical signal into a second optical signal. In this embodiment it is possible to continuously transmit parameter values acquired by the sensor system to a signal processing unit outside the container without the need of additional wiring. This is particularly useful when the application of a correct dosage shall be monitored during the delivery of the medicament.

In a further embodiment of the invention the sensor system comprises a sensor for measuring the pressure in the fluid medicament. The variation of the pressure in the course of the delivery of the fluid medicament characterises a normal, intended delivery process versus the occurrence of an occlusion or a leak along the delivery line. Therefore, this embodiment is particularly advantageous with respect to a safety system to ensure the reliable application of the medicament.

In another embodiment the sensor system comprises a sensor for measuring the force applied on the fluid medicament by the cooperating delivery device. The force required to push out a fluid medicament with a delivery line in undamaged condition is known or can be determined up to a certain tolerance range. A measured force above this range indicates an occlusion, whereas a measured force beyond this range indicates a leakage. Therefore, a container according to this embodiment is particularly advantageous with respect to a safety system to ensure the reliable application of the medicament.

In one embodiment of the invention the container is a cartridge which is closed in one end by a movable bung and adapted to cooperate with a delivery device comprising a sensor for measuring the displacement of the movable bung during the delivery. According to this embodiment, the variation of a physical or chemical parameter related to the container and/or fluid medicament therein is measured along the movement of the movable bung during the delivery of the medicament. For certain parameters, for instance for the pressure in the fluid medicament or for the force required to push out the fluid medicament, the relationship between the displacement of the bung and said parameter is known or can be determined up to a certain tolerance range for a delivery line in undamaged condition.

In such undamaged condition, as an example, the pressure in the fluid medicament rises substantially linearly when moving the bung so as to push out the medicament until a certain pressure value between a lower pressure limit and an upper pressure limit is reached at a first displacement of the bung. On a further movement of the bung beyond said first displacement, the pressure value remains substantially constant, until a desired dose of the medicament in the cartridge is nearly delivered at a second displacement of the bung. When the bung is moved further beyond said second displacement, the pressure decreases substantially linearly beyond the lower pressure limit, until the cartridge is emptied.

Contrary to this, on the occurrence of a leak along the delivery line, the pressure in the medicament will not reach the lower pressure limit. In the presence of an occlusion, the pressure will not remain constant but excess the upper pressure limit when the bung is moved beyond the first displacement. It is possible to stop the delivery process when a substantial deviation of the measured pressure from a corridor formed by the lower and the upper pressure limit is detected.

With parameter values delivered by a cartridge according to this embodiment of the invention it is therefore possible to determine whether the delivery line is in undamaged condition and, consequently, whether the intended dosage was applied to the patient.

In accordance to a second aspect of the invention, a delivery device for delivering a fluid medicament from a container comprising a sensor system has a control unit. Said control unit comprises an optical radiation source that is designed to emit optical radiation receivable by the optical receiver of the sensor system of the container. It is therefore possible to power the sensor system from the delivery device without the need of a wired connection between the delivery device and the container that would restrict the flexibility in engineering and operating such a delivery device.

In an embodiment it is possible to use a material that is essentially transparent for the optical radiation emitted from the optical radiation source, for instance plastics, for the housing or other parts of the delivery device such that the housing or the other parts form a light guide that guides this optical radiation towards the optical receiver. By this embodiment, the proportion of optical radiation that is actually received by the optical receiver is increased, so that the power consumption of the control unit can be reduced. Furthermore, as a free transmission of the optical radiation in air is not required by this embodiment, a more flexible design of the delivery device is facilitated.

In accordance to a third aspect the invention relates to a delivery device for delivering a fluid medicament from a container, wherein the container comprises a control unit, a piston rod and an electrically operable sensor system for measuring at least one physical or chemical parameter value related to the container and/or the fluid medicament therein. The container is formed as a cartridge which is closed in one end by a movable bung operable by the piston rod. The control unit comprises an optical radiation source. The sensor system is arranged between the piston rod and the movable bung and comprises an optical receiver. Said optical receiver is designed to receive optical radiation energy emitted by the optical radiation source and to transform it into electrical energy for operating the sensor system.

As an advantage, said arrangement enables the sensor system to measure physical parameters within the proximity of the cartridge like, for instance, a pressure force acting on the bung or to detect whether a contact between the bung and the piston rod is obtained or maintained. Said arrangement further enables an optical connection that is particularly stable and particularly efficient with regard to the optical radiation transmitted from the optical radiation source of the control unit towards the optical receiver of the sensor system.

In a further embodiment, the sensor system can be formed as a separable unit that can be mounted at the movable bung of the cartridge or at the piston rod of the delivery device. With this embodiment, it is possible to choose from a variety of different sensor systems measuring different physical or chemical parameters independently from the delivery device and the cartridge. It is furthermore possible to form the sensor system as a disposable, for example in order to ease and improve disinfection.

In a further embodiment according to the third aspect of the invention the control unit is placed in the body of the delivery device and coaxially aligned to the piston rod.

Furthermore, the control unit is controllable by a control logic of the delivery device. In this embodiment, the delivery device may comprise a user interface such as a display and at least one button, which is controlled by a control logic formed as a microcontroller. As the control unit is controlled by the device logic, the sensor system can be configured via the user interface of the delivery device. It is also possible that the control unit issues warnings or error messages via the user interface, in particularity when a potential problem along the fluid medicament delivery line is detected. In this embodiment, it is also possible that software routines of both the control logic and the device logic run on a shared microcontroller.

This embodiment results in a particularly compact design of the delivery device that is easy to handle and operate. As the control unit is coaxially aligned to the piston rod, a direct and stable optical path for transferring the first and the second optical signal can be formed either along or around the piston rod.

In an embodiment according to the third aspect of the invention the optical receiver comprises an optical decoder designed to receive the first optical signal and to transfer the first optical signal into the first electrical signal processable by the sensor system. The optical radiation source comprises an optical encoder designed to send the first optical signal. With this embodiment, it is possible to control the sensor system from the control unit without the need of wiring that would restrict the engineering and operational flexibility of both the delivery device and the cartridge. As an example, it would be possible to choose one particular parameter out of a variety of potentially measurable parameters for further measurements. As a further example, it would be possible to choose a rate or frequency for acquiring values for a parameter to be measured.

In yet another embodiment according to the third aspect of the invention the sensor system comprises an optical transmitter designed to receive the second electrical signal and to transform the second electrical signal into the second optical signal. In this embodiment it is possible to continuously transmit parameter values acquired by the sensor system to a signal processing unit outside the container without the need of additional wiring. This is particularly useful when the application of a correct dosage shall be monitored during the delivery of the medicament.

In an embodiment according to the second or third aspect of the invention the sensor system comprises a sensor for measuring the force applied on the movable bung by the piston rod. As described previously, the force required to push out a fluid medicament with a delivery line in undamaged condition is known or can be determined up to a certain tolerance range. A measured force above this range indicates an occlusion, whereas a measured force beyond this range indicates a leakage. Therefore, a container according to this embodiment is particularly advantageous with respect to a safety system to ensure the reliable application of the medicament.

In another embodiment according to the second or third aspect of the invention the delivery device comprises a sensor for measuring the displacement of the movable bung and/or of the piston rod. As described previously, for certain parameters, for instance for the pressure in the fluid medicament or for the force required to push out the fluid medicament, the relationship between the displacement of the bung and said parameter is known or can be determined up to a certain tolerance range for a delivery line in undamaged condition. This embodiment of the invention thus enables the detection of a damaged condition, for instance an occlusion or a leakage, of the delivery line.

In a further embodiment of the invention the delivery device comprises a signal processing unit designed to receive and process signals emitted via optical radiation by the optical transmitter of the sensor system. With this embodiment it is possible to continuously receive parameter values measured by the sensor system. The processing of said continuously acquired parameter values enables the detection of a damaged condition of the delivery line. It is also possible to process said parameters in a controller that is integrated with or in close proximity to the signal processing unit. Thus a safety system to sense an occlusion or a leak during the delivery can be closely integrated into the delivery device so that both the manufacturing and the handling of the delivery device are improved and eased.

In an embodiment the signal processing unit comprises a photoelement. Such photoelements are available at low cost for a wide range of optical radiation. Such photoelements are also available in miniaturized types that can be integrated with other electronic components of the signal processing unit, resulting in a compact circuitry with a low footprint.

In a further embodiment the control unit and the optical radiation source are integrated. Thus it is possible to coordinate the operation of the sensor system supplied with power and potentially controlled from the optical radiation source with the operation of the signal processing unit processing parameter values acquired by the sensor system. The integration of the control unit and the optical radiation source enables the construction of a more compact delivery device that is easier to handle and maintain.

In a further embodiment the optical radiation emitted from the optical radiation source towards the optical receiver and the optical radiation emitted from the optical transmitter towards the signal processing unit share the optical path or parts thereof. Thus, the number of parts and the complexity of the manufacturing and/or the handling of the delivery device can be reduced even further.

In yet another embodiment the optical radiation source comprises a light emitting device. Such light emitting devices, for example laser diodes or light-emitting diodes, are available at low cost for a wide power and spectral range of optical radiation. Light emitting devices that emit light with a wavelength in the range from about 100 nanometers to about 2000 nanometers are particularly useful for this embodiment. For some applications it may be useful to use light emitting devices that emit non-visible light in order to not detract the user from operating the delivery device. For other applications it may be useful to use visible light as an indication of the correct operation of the sensor system and/or the control unit. Preferably, the wavelength of the light emitting device is also adjusted to the transmission characteristics of the optical path between the control unit and the sensor system.

Such light emitting devices provide a relatively high efficiency for the transformation of electrical energy into optical radiation. They are furthermore available in miniaturized types. Thus, highly compact delivery devices with a particularly low power consumption can be constructed in this embodiment.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1:
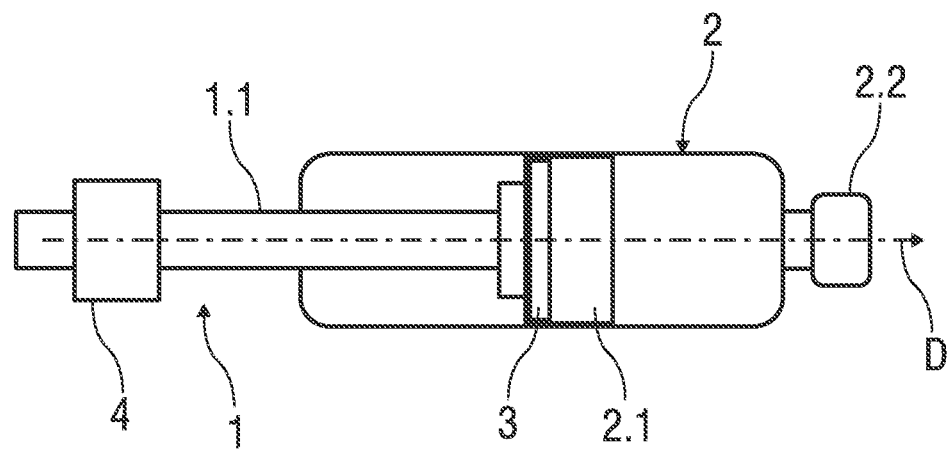
FIG. 1 schematically shows a sensor system arranged between a piston rod of a delivery device and a movable bung of a cartridge, FIG. 2 schematically shows a sensor system integrated in container formed as a cartridge, FIG. 3 schematically shows a circuitry of a sensor system and a control unit and FIG. 4 schematically shows courses of the pressure inside a cartridge versus the displacement of the movable bung during a delivery with and without an occlusion or leakage.

FIG. 1 shows a delivery device 1 that comprises a piston rod 1.1. The piston rod 1.1 is movable along the axis of a push-out direction D of a container 2. The container 2 is formed as a cartridge with a movable bung 2.1. When moved in the push-out direction D, the movable bung 2.1 forces a fluid medicament inside the cartridge 2 through the outlet 2.2.

The piston rod 1.1 acts onto the movable bung 2.1 in order to move it. A sensor system 3 is arranged between the piston rod 1.1 and the movable bung 2.1. Thus, the pressure force applied by the piston rod 1.1 onto the movable bung 2.1 can be measured by the sensor system 3. The sensor system 3 can also be formed as a contact sensor that detects whether a contact between the movable bung 2.1 and the piston rod 1.1 is obtained or maintained.

The delivery device 1 may also comprise at least one further sensor that is not shown here to determine the displacement of the movable bung 2.1. The delivery device 1 may further comprise a device logic that transfers measurement values of the movable bung 2.1 towards the control unit 4.

The movable bung 2.1 can also be made from a material such as glass or plastic that is essentially transparent for the optical signals 5.1, 5.2. Then it is possible to measure physical or chemical parameters of the medicament with the sensor system 3. For example, it is possible to determine the extinction of an optical spectrum emitted by the sensor system 3 in order to identify and/or quantify specific substances in the cartridge 2. It would also be possible to identify and/or quantify a substance in the cartridge 2 by means of fluorescence detected by the sensor system 3.

A control unit 4 is coaxially aligned to the piston rod 1.1. It is possible to fixate the control unit 4 so as to prevent a movement relative to the piston rod 1.1 along the push-out direction D in order to improve the handling. It is also possible to control the control unit 4 by a control logic of a delivery device 1 that is automatically controlled or operated.

The piston rod 1.1 may be made of a material such as glass or plastic that is essentially transparent for the optical signals 5.1, 5.2. Then it is possible to use the piston rod 1.1 also as a light guide for transmitting optical radiation between the sensor system 3 and the control unit 4 with particularly low losses.

Figure 2:
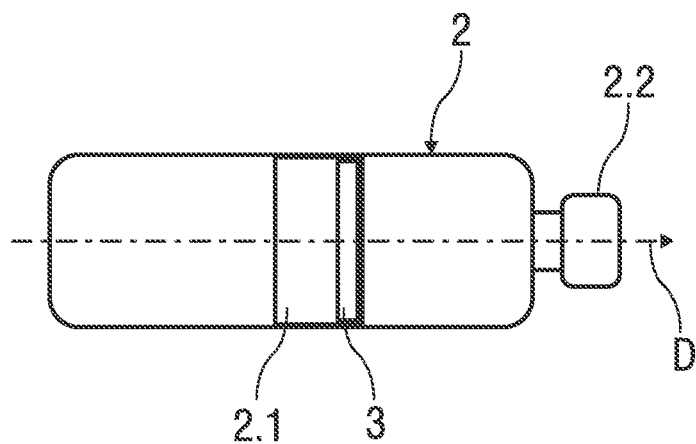

FIG. 2 shows a container 2 that is formed as a cartridge with a movable bung 2.1. A sensor system 3 is arranged inside the cartridge 2. The sensor system 3 can be arranged on the movable bung 2.1 facing the outlet 2.2 as shown in FIG. 2. The movable bung 2.1 is made of a material such as glass or plastic that is essentially transparent for the optical signals 5.1, 5.2, so that an optical path through the movable bung 2.1 is established that optically connects the sensor system 3 with a control unit 4 outside the cartridge 2.

In a particularly useful variation of this embodiment the sensor system 3 is formed as to measure the pressure that is applied by the movable bung 2.1 onto the medicament inside the cartridge 2. This embodiment is also useful for measuring parameters that require immediate contact between a sensor system 3 and a medicament, as for instance pH value or conductance.

Figure 3:
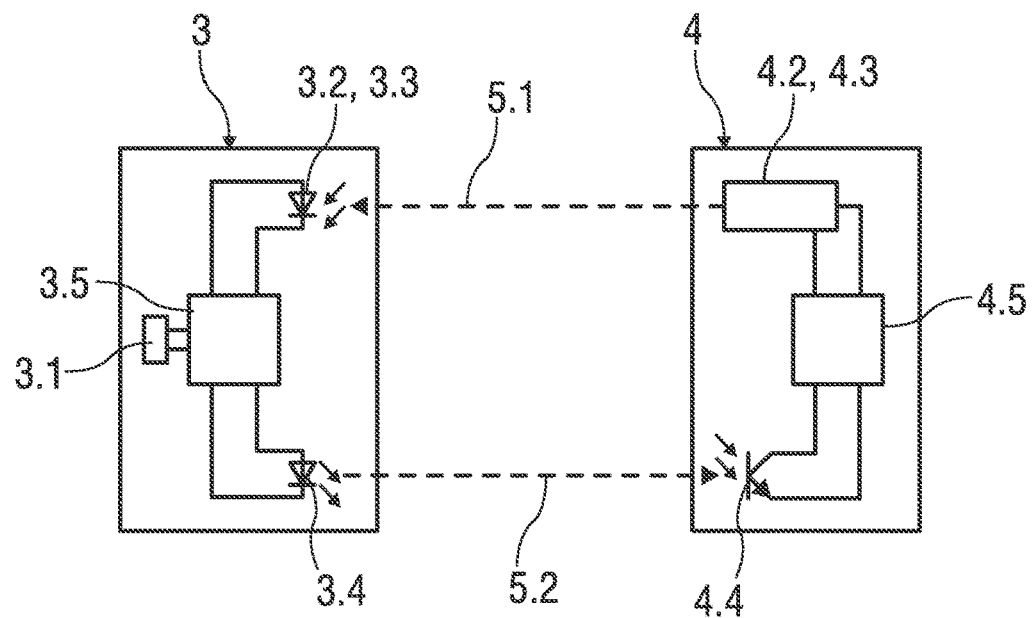

FIG. 3 schematically shows a circuitry of the sensor system 3 and the control unit 4. The sensor system 3 comprises a sensor 3.1 that is designed to measure at least one physical or chemical parameter. As an example, the sensor 3.1 could be formed as a capacitive sensor to measure a force or a pressure acting upon the sensor. The sensor 3.1 could also be formed as a strain gauge to measure a displacement or deformation. The sensor 3.1 could furthermore be formed as a thermoresistor to measure a temperature.

The sensor system 3 further comprises an optical receiver 3.2 for receiving optical radiation and converting it into electrical energy. As an example, the optical receiver 3.2 can be formed as a photoelement.

Furthermore, the sensor system 3 comprises an optical transmitter 3.4. The optical transmitter 3.4 transforms an electrical signal into optical radiation. It can, for instance, be formed as a light emitting diode.

The control unit 4 is optically connected with the sensor unit 3 so that a first optical signal 5.1 is transferable from the optical radiation source 4.2 to the optical receiver 3.2. The sensor unit 3 is optically connected with the control unit 4 so that a second optical signal 5.2 is transferable from the optical transmitter 3.4 to a signal processing unit 4.4 of the control unit 4. An optical connection can be achieved by a directed transmission of optical radiation, for instance by a system of lenses or by a lightguide. It is possible that the optical connection from the sensor unit 3 towards the control unit 4 and the optical connection from the control unit 4 towards the sensor unit 3 share a system of lenses or a light guide, or parts thereof. In an embodiment according to FIG. 1 it is possible to use the piston rod 1.1 or parts thereof as a lightguide for both optical connections.

The sensor 3.1, the optical receiver 3.2 and the optical transmitter 3.4 are electrically connected with a control logic 3.5. Via this electrical connection, the sensor 3.1, the optical transmitter 3.4 and the control logic 3.5 are powered by the electrical energy delivered by the optical receiver 3.2. In an embodiment, it is also possible to transfer a first electrical signal via the electrical connection between the optical receiver 3.2 and the control logic 3.5. The control logic 3.5 acquires a measurement value from the sensor 3.1 and controls via a second electrical signal the optical transmitter 3.4 so as to encode and transmit the parameter value via optical radiation as a second optical signal 5.2.

The control unit 4 comprises an optical radiation source 4.2 that can be formed as a laser diode, as a light emitting diode or as some other device emitting light. The control unit 4 furthermore comprises a signal processing unit 4.4 that receives the second optical signal 5.2, decodes it and converts it into a third electrical signal. Both the signal processing unit 4.4 and the optical radiation source 4.2 are electrically connected with a control logic 4.5.

The acquisition of parameter values proceeds as follows: the control logic 4.5 powers the optical radiation source 4.2. The optical radiation emitted by the optical radiation source 4.2 is received by the optical receiver 3.2. There, the optical radiation is converted into electrical energy that powers the sensor 3.1, the optical transmitter 3.4 and the control logic 3.5 of the sensor system 3.

The sensor 3.1 acquires a parameter value and transmits it towards the control logic 3.5. The control logic 3.5 processes the parameter value. As an example, the average value of a number of sequentially acquired parameter values may be calculated. As another example, a minimum or a maximum out of a number of sequentially acquired parameter values may be determined. The control logic 3.5 transmits the processed parameter value to the optical transmitter 3.4 as a second electrical signal.

The optical transmitter 3.4 converts the second electrical signal into a second optical signal 5.2. For example, the optical radiation emitted by the optical transmitter 3.4 can be pulse-width modulated, i.e. varied in the duration of sequentially emitted light pulses. As another example, the optical radiation emitted by the optical transmitter 3.4 can be amplitude-modulated, i.e. varied in its brightness.

The second optical signal 5.2 emitted by the optical transmitter 3.4 is received by the signal processing unit 4.4 and decoded into a third electrical signal that is transmitted to the control logic 4.5.

The described procedure can be repeated so that a plurality of sequentially acquired parameter values is available at the control logic 4.5 of the control unit 4.

According to a particularly useful embodiment of the invention, the pressure applied by the piston rod 1.1 on the movable bung 2.1 is one parameter measured by the sensor 3.1. A further parameter assigned to each measured pressure value can be the displacement of the piston rod 1.1 relative to the housing of the cartridge 2.

Figure 4:
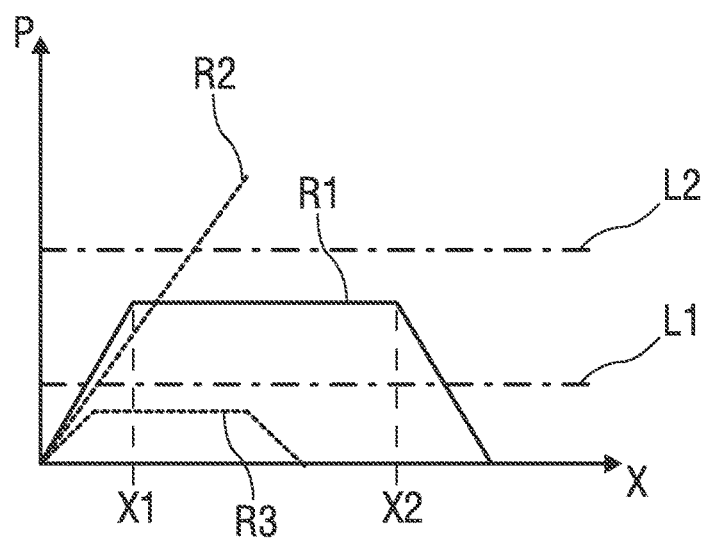

FIG. 4 schematically depicts possible variations R1, R2, R3 of the relationship between pressure values along axis P and displacement values along axis X as they are known or can be determined up to a certain tolerance for different conditions of the delivery line along which a dose of the fluid medicament is delivered from the outlet 2.2 of the cartridge 2 towards a delivery point in the tissue or a vein of a patient.

As shown by the relationship R1 for an undamaged delivery line, the pressure P applied on the movable bung 2.1 rises substantially linearly until the friction force between the movable bung 2.1 and an inner surface of the cartridge 2 is overcome by a pressure above a lower limit L1 at a first displacement X1 of the piston rod 1.1 and the movable bung 2.1 starts to move. On a further movement of the piston rod 2.1 beyond said first displacement X1, the pressure value remains substantially constant, until the dose of the fluid medicament in the cartridge 2 is nearly delivered and the movement of the piston rod 2.1 is stopped at a second displacement X2. The movable bung 2.1 is slightly moved further until it is stopped by the sticking friction force. During the movement of the movable bung 2.1 beyond said second displacement x2, the pressure decreases substantially linearly beyond the lower pressure limit L1, until the dose is delivered completely.

Except for the starting and the stopping of the movable bung 2.1 at the beginning and at the end of the delivery of the dose the pressure applied on the movable bung 2.1 remains within a corridor formed by the lower limit L1 and the upper limit L2 when the delivery line is in an undamaged condition.

Contrary to this, on the occurrence of a leak along the delivery line, the pressure P applied on the movable bung 2.1 will not reach the lower pressure limit L1 as shown by the relationship R3. In the presence of an occlusion, the pressure P will not remain constant but excess the upper pressure limit L2 when the movable bung 2.1 is moved beyond the first displacement X1. In other words: the pressure applied on the movable bung 2.1 will be substantially outside the corridor formed by the lower limit L1 and the upper limit L2 when the delivery line is in damaged condition.

According to these relationships R1, R2, R3, the control logic 4.5 of the control unit 4 is programmed to detect whether the variation of the pressure value measured by the sensor 3.1 falls outside the corridor defined by the lower pressure limit L1 and the upper pressure limit L2 between the first displacement X1 and the second displacement X2. The control logic 4.5 can be programmed to either issue an alarm on any damage condition detected, or to transmit an alarm or status signal towards a supervising controller, as for example a supervising control logic of the delivery device 1.

In an embodiment, the optical receiver 3.2 further comprises an optical decoder 3.3, whereas the optical radiation source 4.2 further comprises an optical encoder 4.3.

According to this embodiment it is possible to control the operation of the sensor system 3. As an example, a specific sampling rate for acquiring the parameter values can be configures as follows. A command to adjust the sampling rate of the sensor 3.1 is transferred from the control logic 4.5 towards the optical encoder 4.3 that converts the electrical signal into a first optical signal 5.1. For example, the optical radiation emitted by the optical encoder 4.3 can be pulse-width modulated, i.e. varied in the duration of sequentially emitted light pulses. As another example, the optical radiation emitted by the optical encoder 4.3 can be amplitude-modulated, i.e. varied in its brightness.

The first optical signal 5.1 emitted by the optical encoder 4.3 is received by the optical decoder 3.3 and converted into a first electrical signal. This first electrical signal is transferred towards the control logic 3.5, which is adapting its frequency of acquiring parameter values from the sensor 3.1 accordingly.

As an advantage of this embodiment, performance and power consumption of the sensor system 3 can be optimized from the control unit 4.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A container designed to contain a fluid medicament and adapted to cooperate with a delivery device for delivering the fluid medicament, wherein the container comprises an electrically operable sensor system for measuring at least one physical or chemical parameter value related to the container and/or the fluid medicament therein, and wherein the sensor system comprises
   (a) an optical receiver designed to receive a first optical signal and to transform said first optical signal into a first electrical signal processable by the sensor system, and
   (b) an optical transmitter designed to receive a second electrical signal and to transform the second electrical signal into a second optical signal;
   wherein the container is closed on one end by a movable bung, wherein the movable bung is composed of a material that is essentially transparent, and
   wherein the sensor system is positioned such that the first optical signal and the second optical signal follow respective optical paths through at least a portion of the movable bung.

2. A container according to claim 1, wherein the optical receiver comprises an optical decoder designed to receive the first optical signal and to transfer the first optical signal into the first electrical signal processable by the sensor system.

3. A container according to claim 1, wherein the sensor system comprises a sensor for measuring a pressure in the fluid medicament.

4. A container according to claim 1, wherein the sensor system comprises a sensor for measuring a force applied on the fluid medicament by the cooperating delivery device.

5. A delivery device for delivering a fluid medicament from a container according to claim 1, wherein the delivery device comprises a control unit comprising an optical radiation source designed to emit optical radiation receivable by the optical receiver of the container.

6. A delivery device according to claim 5, wherein the sensor system comprises a sensor for measuring a force applied on the movable bung by the piston rod.

7. A delivery device according to claim 5, further comprising a signal processing unit designed to receive and process the second optical signal, wherein the signal processing unit comprises a photoelement.

8. A delivery device according to claim 5, wherein the control unit and the optical radiation source are integrated.

9. A delivery device according to claim 5, wherein the optical radiation source comprises a light emitting device.

10. The delivery device of claim 5, further comprising a piston rod positioned to engage the movable bung, wherein the control unit is coaxially aligned with the piston rod, and wherein the piston rod is composed of a material that is essentially transparent and forms a respective optical path for each of the first optical signal and the second optical signal.

11. A delivery device for delivering a fluid medicament from a container comprising
   a piston rod,
   an electrically operable sensor system for measuring at least one physical or chemical parameter value related to the container and/or the fluid medicament therein, wherein the container is a cartridge which is closed in one end by a movable bung operable by the piston rod, and wherein the sensor system is arranged between the piston rod and the movable bung, and
   a control unit, wherein the control unit comprises an optical radiation source, wherein the sensor system comprises an optical receiver designed to receive optical radiation energy emitted by the optical radiation source and to transform said optical radiation energy into electrical energy for operating the sensor system, and wherein the control unit comprises a signal processing unit designed to receive and process an optical signal from the sensor system.

12. A delivery device according to claim 11, wherein the control unit is placed in a body of the delivery device and coaxially aligned to the piston rod and wherein the control unit is controllable by a control logic of the delivery device.

13. A delivery device according to claim 11, wherein the optical signal is a second optical signal, wherein the optical receiver comprises an optical decoder designed to receive a first optical signal and to transform the first optical signal into a first electrical signal processable by the sensor system and wherein the optical radiation source comprises an optical encoder designed to send the first optical signal.

14. A delivery device according to claim 13, wherein the sensor system comprises an optical transmitter designed to receive a second electrical signal, transform the second electrical signal into the second optical signal, and transmit the second optical signal.

15. The delivery device of claim 11, wherein the control unit is coaxially aligned with the piston rod, and wherein the piston rod is composed of a material that is essentially transparent and forms an optical path for the optical radiation energy along the piston rod.

16. A method for monitoring a delivery device, the delivery device comprising, a piston rod,
   an electrically operable sensor system for measuring at least one physical or chemical parameter value related to the container and/or the fluid medicament therein, wherein the container is a cartridge which is closed in one end by a movable bung operable by the piston rod, and wherein the sensor system is arranged between the piston rod and the movable bung, and
   a control unit, wherein the control unit comprises an optical radiation source, wherein the sensor system comprises an optical receiver designed to receive optical radiation energy emitted by the optical radiation source and to transform said optical radiation energy into electrical energy for operating the sensor system, and wherein the control unit comprises a signal processing unit designed to receive and process an optical signal from the sensor system,
   the delivery device adapted for delivering fluid medicament from a container designed to contain a fluid medicament and adapted to cooperate with a delivery device for delivering the fluid medicament, wherein the container comprises an electrically operable sensor system for measuring at least one physical or chemical parameter value related to the container and/or the fluid medicament therein, and wherein the sensor system comprises
   (a) an optical receiver designed to receive a first optical signal and to transform said first optical signal into a first electrical signal processable by the sensor system, and
   (b) an optical transmitter designed to receive a second electrical signal and to transform the second electrical signal into a second optical signal;
   wherein the container is closed on one end by a movable bung, wherein the movable bung is composed of a material that is essentially transparent, and
   wherein the sensor system is positioned such that the first optical signal and the second optical signal follow respective optical paths through at least a portion of the movable bung,
   wherein the sensor system comprises a sensor for measuring a pressure in the fluid medicament, and
   wherein the variation of the pressure in the fluid medicament during delivery is determined and an alarm or a status signal is issued by the control unit when the determined pressure value deviates from a predefined relationship for an undamaged delivery line.

17. A container designed to contain a fluid medicament and adapted to cooperate with a delivery device for delivering the fluid medicament,
   wherein the container comprises an electrically operable sensor system for measuring at least one physical or chemical parameter value related to the container and/ or the fluid medicament therein, and
   wherein the sensor system is arranged inside the container and comprises
   (a) an optical receiver designed to receive optical radiation energy emitted by an optical radiation source and to transform said optical radiation energy into electrical energy for operating the sensor system, (b) a sensor adapted to measure at least one physical or chemical parameter, and
(c) an optical transmitter designed to receive an electrical signal from the sensor and to transform the electrical signal into an optical signal and to optically transmit it.

18. A delivery device adapted to cooperate with a container for delivering a fluid medicament from the container,
    wherein the container comprises an electrically operable sensor system for measuring at least one physical or chemical parameter value related to the container and/or the fluid medicament therein, and
    wherein the sensor system is arranged inside the container and comprises
    (a) an optical receiver designed to receive optical radiation energy emitted by an optical radiation source and to transform said optical radiation energy into electrical energy for operating the sensor system,
    (b) a sensor adapted to measure at least one physical or chemical parameter, and
    (c) an optical transmitter designed to receive an electrical signal from the sensor and to transform the electrical signal into an optical signal and to optically transmit it,
    the delivery device comprising a control unit comprising an optical radiation source designed to emit optical radiation receivable by the optical receiver of the container.

* * * * *